United States Patent
Kim et al.

(10) Patent No.: US 11,883,686 B2
(45) Date of Patent: Jan. 30, 2024

(54) APPARATUS AND METHOD FOR VERIFYING RADIATION DOSE USING PATIENT-SPECIFIC TUMOR-SHAPED SCINTILLATION

(71) Applicant: IUCF-HYU (Industry-University Cooperation Foundation Hanyang University), Seoul (KR)

(72) Inventors: Yong Kyun Kim, Sejong (KR); Hyun Tai Chung, Seoul (KR); Jun Sik Park, Gunpo-si (KR); Jae Bum Son, Namyangju-si (KR); Sang Min Lee, Seoul (KR); Dong Geon Kim, Goyang-si (KR); Tae Hoon Kim, Seoul (KR); Jae Young Jeong, Seoul (KR)

(73) Assignee: IUCF-HYU (Industry-University Cooperation Foundation Hanyang University), Seoul (KR)

( * ) Notice: Subject to any disclaimer, the term of this patent is extended or adjusted under 35 U.S.C. 154(b) by 20 days.

(21) Appl. No.: 17/635,411

(22) PCT Filed: Sep. 4, 2019

(86) PCT No.: PCT/KR2019/011388
§ 371 (c)(1),
(2) Date: Feb. 15, 2022

(87) PCT Pub. No.: WO2021/033823
PCT Pub. Date: Feb. 25, 2021

(65) Prior Publication Data
US 2022/0273967 A1    Sep. 1, 2022

(30) Foreign Application Priority Data
Aug. 16, 2019   (KR) ........................ 10-2019-0100143

(51) Int. Cl.
*A61N 5/10*        (2006.01)
*G01T 1/161*       (2006.01)

(52) U.S. Cl.
CPC ......... *A61N 5/1071* (2013.01); *A61N 5/1031* (2013.01); *G01T 1/161* (2013.01); *A61N 2005/1034* (2013.01)

(58) Field of Classification Search
CPC .............. A61N 5/1071; A61N 5/1031; A61N 2005/1034; G01T 1/161; G01T 1/023; G01T 7/005
See application file for complete search history.

(56) References Cited

U.S. PATENT DOCUMENTS

| 3,536,914 A | * | 10/1970 | Chapman .................. G01T 1/02 |
| | | | 250/367 |
| 2003/0212325 A1 | * | 11/2003 | Cotrutz ................ A61N 5/1031 |
| | | | 600/436 |

(Continued)

FOREIGN PATENT DOCUMENTS

| KR | 10-1378875 B1 | 3/2014 |
| KR | 10-1717728 B1 | 3/2017 |

(Continued)

OTHER PUBLICATIONS

Kim, T. H. et al.,, "Development of a 3-D printed tumor-shaped scintillator measurement system", Transactions of the Korean Nuclear Society Spring Meeting Jeju, May 23-24, 2019, p. 1-2 introduction; methods; results; conclusion; figures 1-4.

*Primary Examiner* — Marcus H Taningco
(74) *Attorney, Agent, or Firm* — NKL Law; Jae Youn Kim (57) ABSTRACT

Proposed is an apparatus for verifying a radiation dose using a patient-specific tumor-shaped scintillator including a probe adapter to which a 3D tumor-shaped scintillator having a guide is attached; a receiving portion to which the probe (Continued)

adapter is detachably coupled; a light guide which extends from the receiving portion and includes optical fiber transmitting visible light generated by irradiating radiation in the 3D tumor-shaped scintillator; a photomultiplier tube converting the visible light transmitted from the light guide into an electric signal and amplifying the converted electric signal; and a current electrometer measuring an output current by inputting the electric signal of the photomultiplier tube.

9 Claims, 7 Drawing Sheets

(56)  References Cited

U.S. PATENT DOCUMENTS

2016/0279445 A1*  9/2016  Ju .................. A61N 5/1039
2022/0249033 A1*  8/2022  Followill ............ G06T 5/005

FOREIGN PATENT DOCUMENTS

KR    10-2018-0060968 A    6/2018
KR    10-2019-0030150 A    3/2019

* cited by examiner

APPARATUS AND METHOD FOR VERIFYING RADIATION DOSE USING PATIENT-SPECIFIC TUMOR-SHAPED SCINTILLATION

CROSS-REFERENCE TO RELATED APPLICATION

This application is a national stage application of PCT PCT/KR2019/011388, filed Sep. 4, 2022, which claims priority KR 10-2019-0100143, filed Aug. 16, 2019, the entire disclosure of which is incorporated herein by reference.

BACKGROUND

(a) Technical Field

The present disclosure relates to an apparatus and a method for verifying a radiation dose using a patient-specific tumor-shaped scintillator.

The national R&D project supporting the present disclosure has a project specific number of 201800000002669, a department name of the Ministry of Science and ICT, a research management specialized institute of the National Research Foundation of Korea, a radiation technology development project/radiation fusion technology development/radiation fusion technology development (commercialization), a research project name of development of 3D printing plastic scintillator and research on treatment dose measurement, and a managing department of Hanyang University Industry-University Cooperation Foundation.

(b) Background Art

With the development of medical technology, the number of cancer patients in modern times is gradually increasing due to various factors such as early diagnosis of cancer. A radiation treatment technology is a technology that has been widely used in cancer treatment in addition to chemotherapy, surgery, and the like, and is a technology for treating cancer by irradiating radiation to cancer cells to suppress the growth of cancer cells and cause necrosis of cancer cells.

It is important to irradiate a patient with an appropriate radiation dose in order to maximize a radiation treatment effect and reduce the side effects caused by the treatment. For this reason, recently, methods such as intensity modulated radiation treatment (IMRT) have been in the spotlight to adjust the radiation dose irradiated to the patient according to the shape and size of the tumor by using a multi-leaf collimator (MLC).

During the radiation treatment, the radiation dose to be irradiated to the tumor is simulated through medical images of the patient to establish a treatment plan, and the actual radiation dose is measured and verified. As the most common method for verifying the treatment plan of precision radiation treatment equipment, including intensity-controlled radiation treatment, which is currently a main axis of advanced radiation treatment, there is a method of using an ionization chamber.

This is to measure absolutely some dotted absorbed dose at several points in a radiation field using an ionization chamber and measure a relative absorbed dose distribution in several planes in the radiation field using a radiochromic film, which is then compared with the treatment plan.

As such, since the method which has been currently used to verify the radiation treatment plan may only evaluate the treatment dose in one or two dimensions, it is difficult to evaluate an accurate dose when verifying the treatment plan of a radiation treatment device that is irradiated with a dose in a three dimension, such as intensity-controlled radiation treatment. Therefore, there is a need for a method for verifying a radiation dose capable of evaluating the dose in the three dimensions.

The present applicant has proposed manufacturing a patient-specific tumor model through 3D printing in Korean Laid-open Patent Publication No. 10-2019-0030150.

There is a need for a method capable of absolutely measuring the total radiation dose absorbed in the tumor other than the absorbed dose at a specific point in the tumor by using the 3D scintillator manufactured as described above.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

In order to solve the problems in the related art, there are provided an apparatus and a method for verifying a radiation dose using a patient-specific tumor-shaped scintillator capable of absolutely measuring the total radiation dose absorbed in the tumor.

According to an aspect of the present disclosure, there is provided an apparatus for verifying a radiation dose using a patient-specific tumor-shaped scintillator including a probe adapter to which a 3D tumor-shaped scintillator having a guide is attached; a receiving portion to which the probe adapter is detachably coupled; a light guide which extends from the receiving portion and includes optical fiber transmitting visible light generated by irradiating radiation in the 3D tumor-shaped scintillator; a photomultiplier tube converting the visible light transmitted from the light guide into an electric signal and amplifying the converted electric signal; a current electrometer measuring an output current by inputting the electric signal of the photomultiplier tube; and a processor which is connected to a memory storing program instructions, and calculates a dose absorbed in the 3D tumor-shaped scintillator when a plurality of calibration shots are irradiated through Monte Carlo simulation, determines a calibration factor for converting the output current into the dose, and calculates a total dose absorbed in the 3D tumor-shaped scintillator by irradiating radiation used in a treatment plan using the determined calibration factor.

The processor may determine calibration factors for different tumor-shaped scintillators.

A reflector and a black paint may be coated on the surface of the 3D tumor-shaped scintillator, after the measurement of the first output current for the 3D tumor-shaped scintillator is completed, a probe head formed of only the black paint may be attached to the probe adapter to measure a second output current by Cherenkov light, and the processor may determine the calibration factor using an output current obtained by subtracting the second output current from the first output current.

The processor may calculate a total dose absorbed in the 3D tumor-shaped scintillator by multiplying the determined calibration factor by the output current corresponding to visible light generated by irradiating the radiation in the 3D tumor-shaped scintillator when a plurality of plan shots used in the treatment plane is irradiated.

The Monte Carlo simulation may be performed using a phase-space dataset of gamma knife lengths of 4, 8, and 16 mm.

The processor may determine the calibration factor by linearly fitting the output current by the plurality of calibration shots and the dose calculated by the Monte Carlo simulation.

According to another aspect of the present disclosure, there is provided an apparatus for verifying a radiation dose using a patient-specific tumor-shaped scintillator including a processor; and a memory connected to the processor, wherein the memory stores program instructions executable by the processor to calculate a dose absorbed in a 3D tumor-shaped scintillator when a plurality of calibration shots are irradiated through Monte Carlo simulation, measure an output current corresponding to visible light generated by the 3D tumor-shaped scintillator attached to a modular dose verification device, determine a calibration factor for converting the output current into the dose, and calculate a total dose absorbed in the 3D tumor-shaped scintillator by irradiating radiation used in a treatment plan using the determined calibration factor.

According to yet another aspect of the present disclosure, there is provided a method for verifying a radiation dose using a patient-specific tumor-shaped scintillator including the steps of: attaching a 3D tumor-shaped scintillator having a guide to a probe adapter; coupling the probe adaptor to a receiving portion; irradiating a plurality of calibration shots to the 3D tumor-shaped scintillator; converting visible light generated by the 3D tumor-shaped scintillator into an electric signal by the plurality of calibration shots and amplifying the converted electric signal; measuring an output current using the electric signal; calculating a dose absorbed in the 3D tumor-shaped scintillator when the plurality of calibration shots are irradiated through Monte Carlo simulation; determining a calibration factor for converting the output current into the dose; and calculating a total dose absorbed in the 3D tumor-shaped scintillator by irradiating radiation used in a treatment plan using the determined calibration factor.

According to still another aspect of the present disclosure, there is provided a method for verifying a radiation dose using a patient-specific tumor-shaped scintillator in an apparatus including a processor and a memory, the method including the steps of: calculating a dose absorbed in a 3D tumor-shaped scintillator when a plurality of calibration shots are irradiated through Monte Carlo simulation; measuring an output current corresponding to visible light generated by the 3D tumor-shaped scintillator attached to a modular dose verification device; determining a calibration factor for converting the output current into the dose; and calculating a total dose absorbed in the 3D tumor-shaped scintillator by irradiating radiation used in a treatment plan using the determined calibration factor.

According to the exemplary embodiment of the present disclosure, there is an advantage of accurately evaluating a total absorbed dose of a 3D tumor-shaped scintillator by determining a calibration factor through a modular dose verification device and simulation.

DETAILED DESCRIPTION

The present disclosure may have various modifications and various exemplary embodiments and specific exemplary embodiments will be illustrated in the drawings and will be described in detail.

However, the present disclosure is not limited to specific exemplary embodiments, and it should be understood that the present disclosure covers all the modifications, equivalents and replacements included within the idea and technical scope of the present disclosure.

Figure 1:
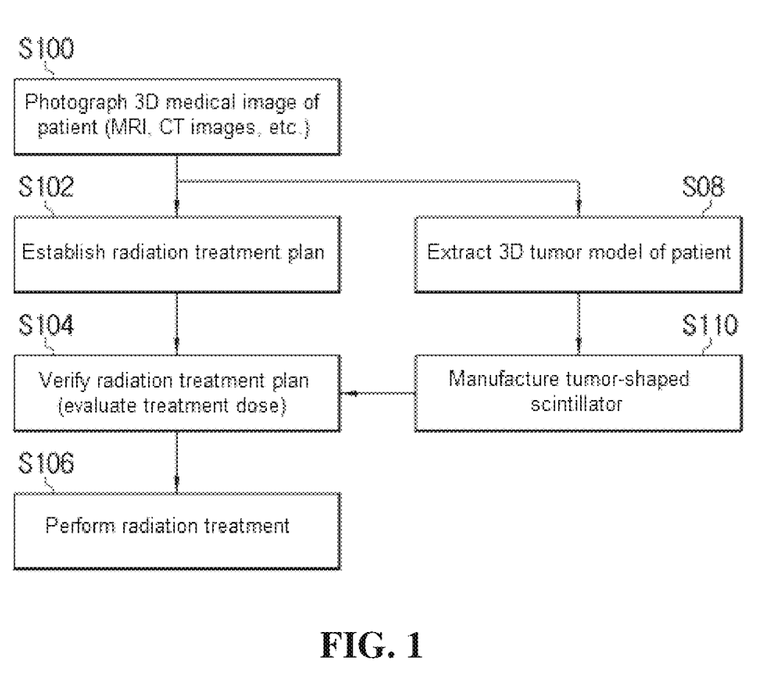
FIG. 1 is a flowchart illustrating a method for verifying a radiation dose using a patient-specific tumor-shaped scintillator according to an exemplary embodiment of the present disclosure.

FIG. 1 is a flowchart illustrating a method for verifying a radiation dose using a patient-specific tumor-shaped scintillator according to an exemplary embodiment of the present disclosure.

Referring to FIG. 1, for a method for verifying a radiation dose by manufacturing a patient-specific scintillator, a 3D medical image of a patient is photographed through CT, MRI, and the like (S100).

Thereafter, a radiation treatment plan is established by calculating the radiation dose simulatedly irradiated to a tumor identified through the 3D medical image (S102).

Next, the radiation treatment plan that actually measures and evaluates the planned radiation treatment dose is verified (S104).

According to an exemplary embodiment of the present disclosure, a modular dose verification device is provided to remove Cherenkov light generated by radiation from an optical fiber and determine a calibration factor of converting an output current measured by the modular dose verification device through Monte Carlo simulation into a dose rate.

The dose verification process will be described above below.

After the dose verification is completed, radiation treatment is performed based on the verified plan (S106).

In this radiation treating process, according to an exemplary embodiment of the present disclosure, a 3D tumor model of a patient is extracted (S108), and a patient-specific tumor-shaped scintillator is manufactured (S110).

Figure 2:
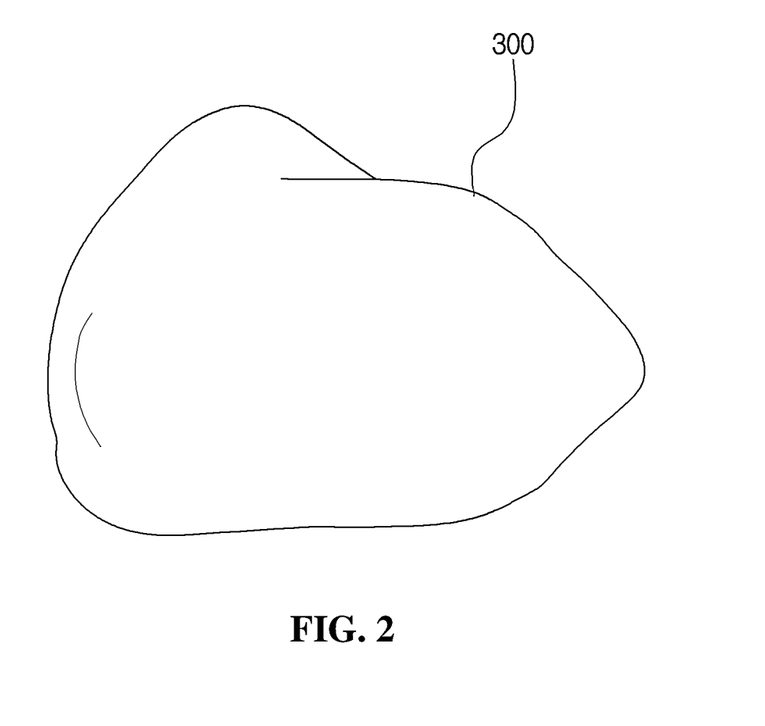
FIG. 2 is a diagram illustrating a patient-specific tumor-shaped scintillator manufactured through 3D printing according to an exemplary embodiment of the present disclosure.
Figure 3:
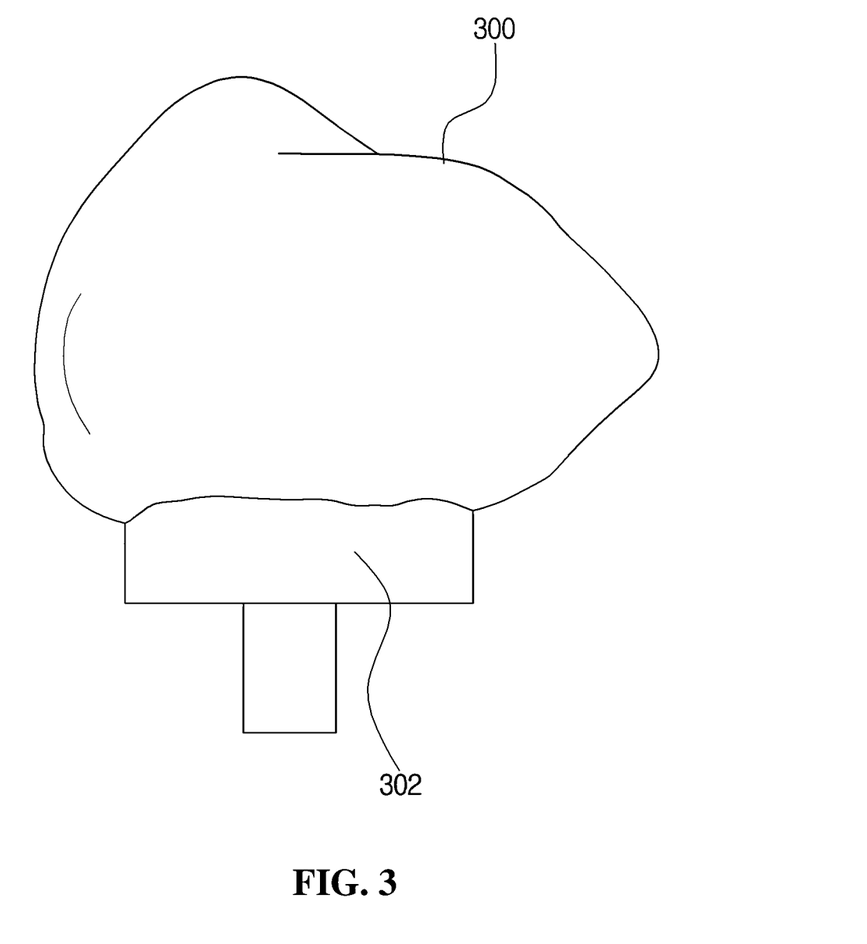
FIG. 3 is a diagram illustrating a state where the tumor-shaped scintillator of FIG. 2 is attached to a guide to be fixed and used to a modular dose verification device.

FIG. 2 is a diagram illustrating a patient-specific tumor-shaped scintillator manufactured through 3D printing according to an exemplary embodiment of the present disclosure, and FIG. 3 is a diagram illustrating a state where the tumor-shaped scintillator of FIG. 2 is attached to a guide to be fixed and used to a modular dose verification device.

According to the exemplary embodiment, a tumor-shaped scintillator 300 and a guide 302 may be manufactured through 3D printing, and the center of the guide 302 and the center of gravity of the attachment surface of the tumor-shaped scintillator 300 are aligned to acquire a 3D CAD file of the tumor-shaped scintillator 300 to which the guide 302 is attached without an empty space and acquire a coordinate of the tumor-shaped scintillator at the same time.

The 3D tumor-shaped scintillator according to the exemplary embodiment may be formed of a plastic scintillator, and may be manufactured by a DLP method of curing and laminating single layers with several-μm thicknesses by irradiating ultraviolet light with certain wavelength and intensity to a liquid plastic scintillator resin.

In general, the radiation treatment is performed by photographing a 3D medical image of the patient, establishing a radiation treatment plan (evaluating a radiation treatment dose), and performing the radiation treatment, and 1D or 2D dose evaluation is performed by using an ionization chamber, a film, or the like when verifying the radiation treatment plan.

Referring to FIG. 1, the method for verifying the radiation dose according to the exemplary embodiment provides a method capable of absolutely measuring a total radiation dose absorbed in the tumor using the 3D scintillator.

By configuring as described above, in the method for verifying the radiation dose by manufacturing the patient-specific scintillator according to an exemplary embodiment of the present disclosure, in addition to the existing 1D and 2D dose evaluation, the 3D dose evaluation is performed, thereby more accurately evaluating the total radiation dose.

In the step (S108) of extracting the 3D tumor model of the patient through the 3D medical image, only the tumor may be defined from a Dicom file as 3D medical image data of the patient to be configured as a 3D model.

CT, MRI, or the like, which is commonly used 3D medical imaging equipment, photographs the human body in 3D to provide slice images of three cross sections such as axial, sagittal, and coronal, and several slice images are laminated to configure a 3D image.

The 3D medical imaging equipment such as CT or MRI mainly stores and provides the photographed medical image data as a Dicom file, and may reconfigure the Dicom file into a 3D image through a 3D medical image analysis program.

Figure 4:
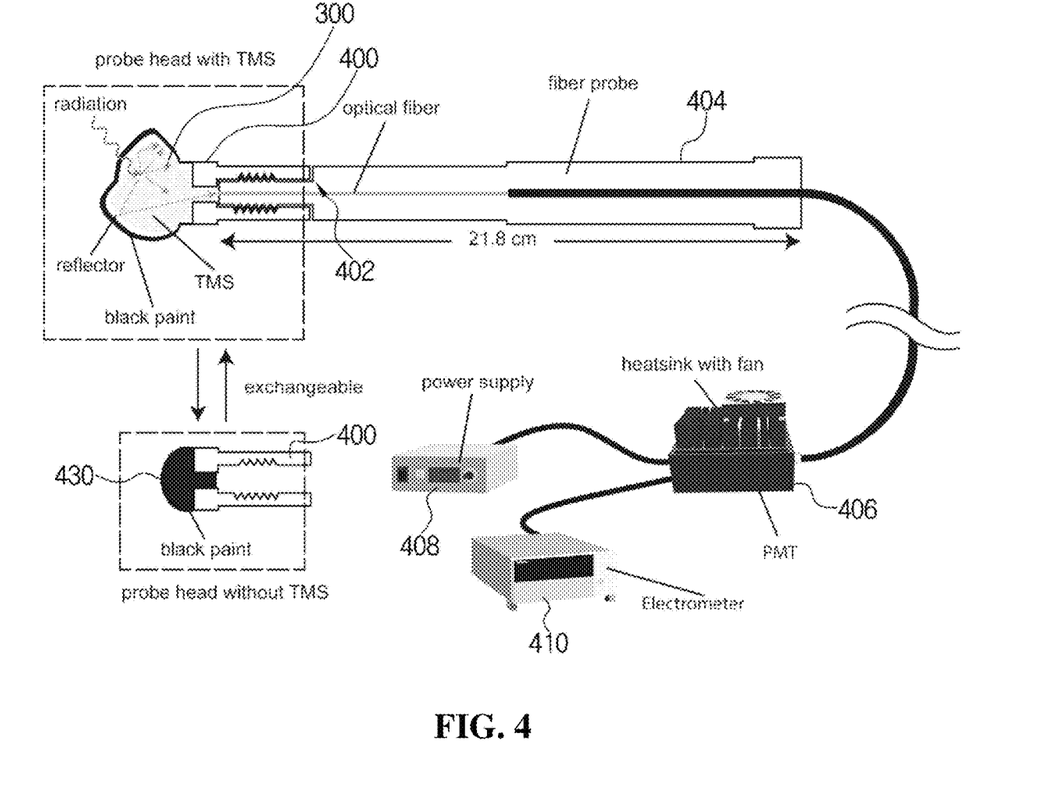
FIG. 4 is a diagram illustrating a configuration of the modular dose verification device according to an exemplary embodiment of the present disclosure.

FIG. 4 is a diagram illustrating a configuration of the modular dose verification device according to an exemplary embodiment of the present disclosure.

Referring to FIG. 4, the modular dose verification device according to the exemplary embodiment may include a probe adapter 400 to which the 3D tumor-shaped scintillator 300 is coupled, a receiving portion 402 receiving the probe adapter 400, a light guide 404 transmitting optical light generated by irradiating radiation in the scintillator 300, a photomultiplier tube (PMT) 406 converting visible light transmitted from the light guide 404 into an electric signal and amplifying the converted electric signal, a power supply 408 supplying power to the PMT, and a current electrometer 410 measuring an output current and a voltage signal of the PMT 406.

The light guide 404 transmitting the optical signal may be formed of acrylic or optical fiber.

The PMT 406 serves to convert the light signal into an electric signal and amplify the converted electric signal on a principle of emitting photoelectrons from a photocathode in the PMT when the light signal emitted from the scintillator 300 is incident, and may be replaced with a multi-anode PMT and the like according to a situation, a condition, and the like.

The signal output from the PMT 406 is stored in a computer through the current electrometer 410 and the computer determines a calibration factor by linear fitting of the output current acquired from the tumor-shaped scintillator 300 attached to the probe adapter 400 and a pre-calculated dose according to the Monte Carlo simulation.

The computer according to the exemplary embodiment may include a processor and a memory.

The processor may include a central processing unit (CPU) capable of executing computer programs, other virtual machines, or the like.

The memory may include a nonvolatile storage device such as a fixed hard drive or a detachable storage device. The detachable storage device may include a compact flash unit, a USB memory stick, etc. The memory may also include volatile memories such as various types of random access memories.

According to an exemplary embodiment of the present disclosure, the processor performs Monte Carlo simulation calculation using program instructions stored in the memory, and determines the calibration factor as described above based on the calculated result.

Figure 5:
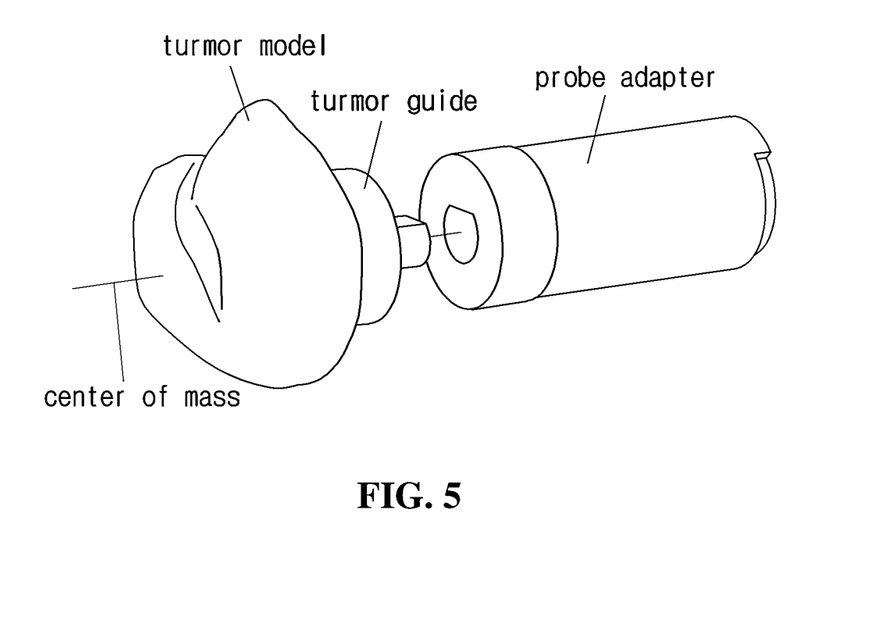
FIG. 5 is a diagram illustrating a process of coupling the scintillator and a probe adapter according to the exemplary embodiment.

FIG. 5 is a diagram illustrating a process of coupling the scintillator and a probe adapter according to the exemplary embodiment.

The 3D tumor-shaped scintillator 300 according to the exemplary embodiment is coupled to a hole 420 formed in the probe adapter 400 through the guide 302.

In addition, a reflector and a block paint are coated on the surface of the scintillator 300.

The probe adapter 400 according to the exemplary embodiment may be provided to be detached to the receiving portion 402 through screw coupling.

To remove Cherenkov light, the probe adapter 400 to which the scintillator 300 is attached is coupled to the receiving portion 402, and then irradiated with radiation and the output current (first output current) of the PMT 406 is measured in the current electrometer 410.

Thereafter, the probe adapter 400 is separated from the receiving portion 402, a probe head 430 formed of only the black paint without the scintillator is provided, and the probe head 430 is attached to the probe adapter 400, and a second output current is measured by irradiating the radiation.

The second output current measured using the probe head 430 formed of only the black paint is due to the Cherenkov light generated from the optical fiber in the light guide 404.

Accordingly, the Cherenkov light may be removed by subtracting the first output current and the second output current.

According to the exemplary embodiment of the present disclosure, a calibration factor is determined by converting the output current generated in the tumor-shaped scintillator 300 and measured in the PMT 406 into a dose using the Monte Carlo simulation calculation.

Figure 6:
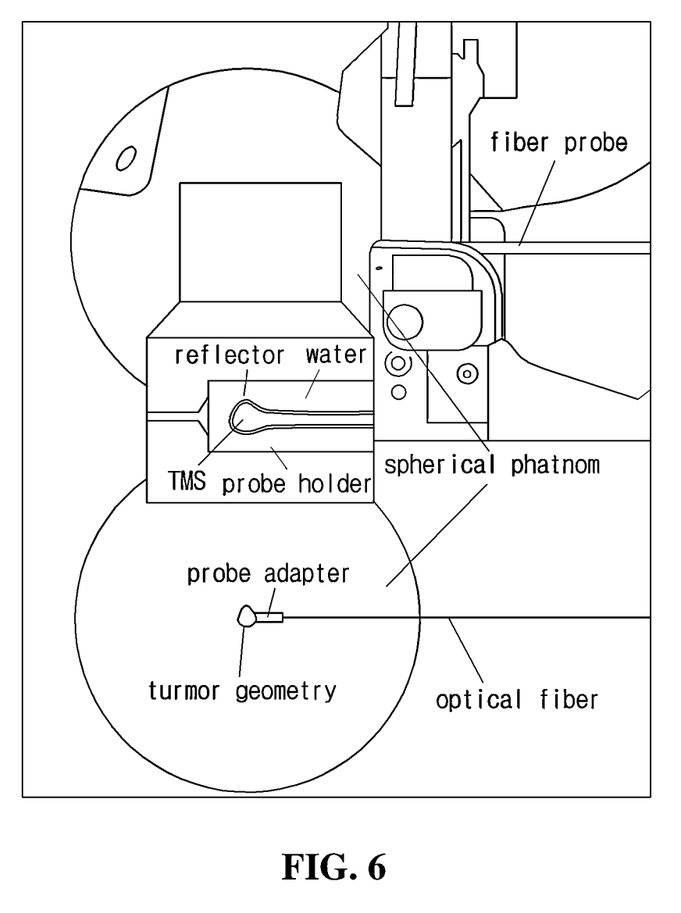
FIG. 6 is a diagram for describing a process of determining a calibration factor according to the exemplary embodiment.

FIG. 6 is a diagram for describing a process of determining a calibration factor according to the exemplary embodiment.

Referring to FIG. 6, the probe adapter 400 to which the tumor-shaped scintillator 300 is attached is inserted into a spherical phantom.

At this time, the tumor-shaped scintillator 300 is positioned at an isocenter of the spherical phantom, and the inside of the probe adapter 400 is fully filled with water to maintain the absence of an air layer.

Thereafter, the radiation is irradiated with to the tumor-shaped scintillator 300 a plurality of calibration shots, and measured for a predetermined time to acquire the uncertainty of an average output current from which the Cherenkov light is removed at a predetermined time interval.

A Geant4 (G4) MC simulation toolkit is used to calculate the dose by the plurality of calibration shots irradiated to the tumor-shaped scintillator 300.

To define the geometry of the tumor in G4, an STL file of the tumor model used for 3D printing was implemented as illustrated in FIG. 6 using CADMesh interface v1.1. The material of the spherical phantom and the tumor volume was set to water and the absorbed dose in the tumor volume is calculated.

A calibration factor according to the corresponding tumor shape is acquired through linear fitting of the output current of a plurality of calibration shots measured in a predetermined tumor shape and the dose rate calculated by Monte Carlo simulation.

To perform the Monte Carlo simulation calculation, the center of the tumor geometry is placed at the center of the spherical phantom, and the plurality of calibration shots are irradiated.

The dose absorbed in the tumor geometry is s calculated using a phase-space dataset of 4, 8, and 16 mm of cobalt 60 gamma knife.

The table below shows 7 calibration shots of Leksell Gamm Knife® (LGK) set to determine the calibration factor.

A coordinate of the center of the shot was set as a coordinate (X=100 mm, Y=100 mm, Z=100 mm) of the LGK helmet center. 4, 8, and 16 mm beams in sectors 1 to 8 may be generated and set as blocked (B) sectors.

Figure 7:
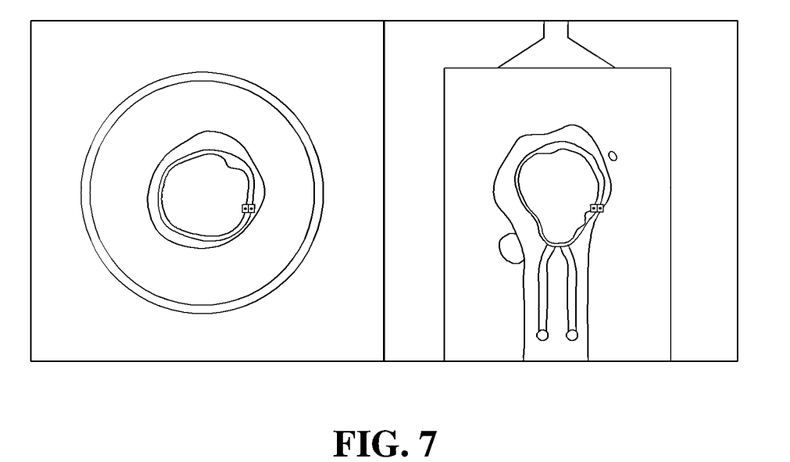
FIG. 7 is a diagram illustrating a treatment plan according to the exemplary embodiment.

As illustrated in FIG. 6, a tumor-shaped scintillator was placed in the center of the spherical phantom to obtain a cone beam computed tomography (CBCT) image, and a treatment plan was prepared as illustrated in FIG. 7.

According to the exemplary embodiment, a treatment plan is established with a plurality of plan shots A1 to A9 for the tumor-shaped scintillator.

As illustrated in FIG. 7, a dose of 8 Gy was prescribed for a 60% isodose line.

Thereafter, the output current of the scintillator by the plan shot is measured. Cherenkov subtraction is performed when the output current is measured.

The calibration factor is applied to the output current from which the Cherenkov light is subtracted to be converted into the dose of the plan shots. In addition, the total dose absorbed by the tumor-shaped scintillator is calculated by applying a calibration factor to a charge amount calculated by integrating the output current from which the Cherenkov light is subtracted for the plan shot into time.

The exemplary embodiments of the present disclosure described above are disclosed for purposes of illustration, and it will be apparent to those skilled in the art that various modifications, additions, and substitutions are possible within the spirit and scope of the present disclosure and these modifications, changes, and additions should be considered as falling within the scope of the following claims.

TABLE 1

| Calibration shots | Isocenter (mm) | | | Sector | | | | | | | | Dose rate at focus (Gy/min) |
|---|---|---|---|---|---|---|---|---|---|---|---|---|
| | X | Y | Z | 1 | 2 | 3 | 4 | 5 | 6 | 7 | 8 | |
| Cal 1 | 100.0 | 100.0 | 100.0 | 4 | 4 | 4 | 4 | 4 | 4 | 4 | 4 | 1.95 |
| Cal 2 | 100.0 | 100.0 | 100.0 | 8 | 8 | 8 | 8 | 8 | 8 | 8 | 8 | 2.15 |
| Cal 3 | 100.0 | 100.0 | 100.0 | 16 | 16 | 16 | 16 | 16 | 16 | 16 | 16 | 2.398 |
| Cal 4 | 100.0 | 100.0 | 100.0 | 16 | B | B | B | B | B | B | B | 0.30 |
| Cal 5 | 100.0 | 100.0 | 100.0 | 16 | 16 | B | B | B | B | B | B | 0.60 |
| Cal 6 | 100.0 | 100.0 | 100.0 | 16 | 16 | 16 | 16 | B | B | B | B | 1.20 |
| Cal 7 | 100.0 | 100.0 | 100.0 | 16 | 16 | 16 | 16 | 16 | 16 | B | B | 1.79 |

According to an exemplary embodiment of the present disclosure, the output current measured by the plurality of calibration shots measured by a predetermined tumor-shaped scintillator and the dose calculated through Monte Carlo simulation are linearly fitted using the following Equation.

$$\dot{D}_{xim}^{cal} = k_{sim} \cdot I_{net}^{cal} \quad \text{[Equation 1]}$$

Wherein, $\dot{D}_{sim}^{cal}$ represents a dose rate calculated by Monte Carlo simulation for a plurality of calibration shots, $k_{xim}$ represents a calibration factor, and $I_{net}^{cal}$ is an output current (output current from which Cherenkov light is removed) measured for the plurality of calibration shots.

According to the exemplary embodiment, calibration factors for different tumor shapes may be determined by irradiating a plurality of calibration shots to different tumor-shaped scintillators.

In a conventional method using an ionization chamber, a uniform calibration factor by a standard institution was applied, but according to the exemplary embodiment, an individual calibration factor according to each tumor shape is determined in order to establish a patient-specific treatment plan. Hereinabove, the gamma knife has been described as an example, but is not limited thereto and the dose verification may also be performed using various radiations.

What is claimed is:

1. An apparatus for verifying a radiation dose using a patient-specific tumor-shaped scintillator comprising:
   a probe adapter to which a 3D tumor-shaped scintillator having a guide is attached;
   a receiving portion to which the probe adapter is detachably coupled;
   a light guide which extends from the receiving portion and includes optical fiber transmitting visible light generated by irradiating radiation in the 3D tumor-shaped scintillator;
   a photomultiplier tube converting the visible light transmitted from the light guide into an electric signal and amplifying the converted electric signal;
   a current electrometer measuring an output current by inputting the electric signal of the photomultiplier tube; and
   a processor which is connected to a memory storing program instructions, and calculates a dose absorbed in the 3D tumor-shaped scintillator when a plurality of calibration shots are irradiated through Monte Carlo simulation, determines a calibration factor for converting the output current into the dose, and calculates a total dose absorbed in the 3D tumor-shaped scintillator by irradiating radiation used in a treatment plan using the determined calibration factor.

2. The apparatus for verifying the radiation dose of claim 1, wherein the processor determines calibration factors for different tumor-shaped scintillators.

3. The apparatus for verifying the radiation dose of claim 1, wherein a reflector and a black paint are coated on the surface of the 3D tumor-shaped scintillator,
after the measurement of the first output current for the 3D tumor-shaped scintillator is completed, a probe head formed of only the black paint is attached to the probe adapter to measure a second output current by Cherenkov light, and
the processor determines the calibration factor using an output current obtained by subtracting the second output current from the first output current.

4. The apparatus for verifying the radiation dose of claim 1, wherein the processor calculates a total dose absorbed in the 3D tumor-shaped scintillator by multiplying the determined calibration factor by the output current corresponding to visible light generated by irradiating the radiation in the 3D tumor-shaped scintillator when a plurality of plan shots used in the treatment plane is irradiated.

5. The apparatus for verifying the radiation dose of claim 1, wherein the Monte Carlo simulation is performed using a phase-space dataset of gamma knife lengths of 4, 8, and 16 mm.

6. The apparatus for verifying the radiation dose of claim 1, wherein the processor determines the calibration factor by linearly fitting the output current by the plurality of calibration shots and the dose calculated by the Monte Carlo simulation.

7. An apparatus for verifying a radiation dose using a patient-specific tumor-shaped scintillator comprising:
a processor; and
a memory connected to the processor,
wherein the memory stores program instructions executable by the processor to calculate a dose absorbed in a 3D tumor-shaped scintillator when a plurality of calibration shots are irradiated through Monte Carlo simulation,
measure an output current corresponding to visible light generated by the 3D tumor-shaped scintillator attached to a modular dose verification device,
determine a calibration factor for converting the output current into the dose, and
calculate a total dose absorbed in the 3D tumor-shaped scintillator by irradiating radiation used in a treatment plan using the determined calibration factor.

8. A method for verifying a radiation dose using a patient-specific tumor-shaped scintillator comprising the steps of:
attaching a 3D tumor-shaped scintillator having a guide to a probe adapter;
coupling the probe adaptor to a receiving portion;
irradiating a plurality of calibration shots to the 3D tumor-shaped scintillator;
converting visible light generated by the 3D tumor-shaped scintillator into an electric signal by the plurality of calibration shots and amplifying the converted electric signal;
measuring an output current using the electric signal;
calculating a dose absorbed in the 3D tumor-shaped scintillator when the plurality of calibration shots are irradiated through Monte Carlo simulation;
determining a calibration factor for converting the output current into the dose; and
calculating a total dose absorbed in the 3D tumor-shaped scintillator by irradiating radiation used in a treatment plan using the determined calibration factor.

9. The method for verifying the radiation dose of claim 8, wherein the output current is obtained by removing the output current by Cherenkov light.

* * * * *